United States Patent [19]

Pasternack

[11] Patent Number: 4,667,669

[45] Date of Patent: May 26, 1987

[54] CYCLE RESPIRATOR FOR PRESSURE OPERATION

[75] Inventor: Adalbert Pasternack, Bad Schwartau, Fed. Rep. of Germany

[73] Assignee: Drägerwerk AG, Fed. Rep. of Germany

[21] Appl. No.: 680,160

[22] Filed: Dec. 6, 1984

[30] Foreign Application Priority Data

Dec. 9, 1983 [DE] Fed. Rep. of Germany ....... 3344567
Aug. 9, 1984 [DE] Fed. Rep. of Germany ....... 3429345

[51] Int. Cl.[4] .......... A61M 16/00

[52] U.S. Cl. .......... 128/204.23; 128/204.28; 128/202.22

[58] Field of Search .......... 128/204.21, 204.23, 128/204.24, 204.25, 205.12, 205.18, 205.14, 205.17, 205.15, 205.16, 202.22

[56] References Cited

U.S. PATENT DOCUMENTS

| | | | |
|---|---|---|---|
| 2,972,345 | 2/1961 | Spigel | 128/204.23 |
| 3,033,195 | 5/1962 | Gilroy et al. | 128/204.21 |
| 3,339,545 | 9/1967 | Burchell | 128/205.14 |
| 3,840,006 | 10/1974 | Buck et al. | 128/204.21 |
| 3,850,170 | 11/1974 | Cox | 128/204.24 |
| 4,036,221 | 7/1977 | Hillsman et al. | 128/204.23 |

FOREIGN PATENT DOCUMENTS

| | | | |
|---|---|---|---|
| 1288019 | 9/1972 | United Kingdom | 128/204.21 |

*Primary Examiner*—Henry J. Recla
*Attorney, Agent, or Firm*—McGlew and Tuttle

[57] ABSTRACT

A cycle respirator for pressure operation makes sure that in the respiratory cycle a positive pressure relative to the ambient atmosphere always prevails. During the exhaling phase this positive pressure is undesirable because he (the user) is additionally burdened unnecessarily during exhalation. The invention includes a sensor connected with a measuring circuit which can distinguish between inhalation phase and exhalation phase and activates through a measuring circuit an auxiliary device by which the positive pressure is reduced during the exhalation phase. Across an electric resistance path a voltage difference drops which varies in accordance with the stroke movements of the breathing bag. This varying voltage difference is used as a measurement signal for the switching of the auxiliary device, whereby the positive pressure in the respiratory cycle is created in the respiratory cycle only during the inhaling phase, but is reduced during the exhaling phase.

8 Claims, 2 Drawing Figures

CYCLE RESPIRATOR FOR PRESSURE OPERATION

FIELD AND BACKGROUND OF THE INVENTION

This invention relates in general to respirators and in particular to a new and useful respirator including an arrangement for reducing the system pressures during exhalation by directing a pressurized gas in a circulating line connected to a breathing bag.

The invention relates to a cycle respirator for pressure operation with a compressed gas source which via a compressed gas line feeds in addition an auxiliary device which by movement of the breathing bag brings about a pressure increase in the respiratory cycle.

Such a cycle respirator is known from German OS No. 31 05 637.

In the known cycle respirator with pressure operation it is made sure that a positive pressure prevails during its use in the respiratory cycle both in the exhaling and in the inhaling phases. This positive pressure prevents during use of the apparatus the penetration of ambient atmosphere which might contaminate it and do harm to the user of the apparatus. Should leaks develop in the respiratory cycle, the created pressure makes sure that there results only a gas stream out of the respiratory cycle into the ambient atmosphere. For the user of the known respirator it means, however, an unnecessary effort that he must make, because a positive pressure is created in the respiratory cycle also during the exhalation phase. The positive pressure required for leakproofness in the sense of protection of the apparatus user is created, in fact, already in the mouthpiece or full mask by the flow resistances following them from the accordian tubes, valves and regeneration cartridges, for example. An additional static pressure burdens the apparatus user additionally and tires him prematurely, The same is true also of the following known compressed gas respirator with positive pressure in the respiratory air according to German Pat. No. 30 15 759, which, too is designed as a cycle apparatus. Here load is applied on a breathing bag disposed in the cycle from the outside by a tensioned spring, the positive pressure being thus maintained in the cycle. From an oxygen pressure vessel the oxygen is supplied to the breathing bag via a lungmotor, which is actuated during evacuation by the movable end wall thereof. The lung-motor is preceded by a shutoff valve which, upon complete evacuation of the breathing bag, is closed by the end wall. Thereby an outflow of large amounts of oxygen is prevented in case of major leaks in the cycle or removal of the mask involving a decrease in the positive pressure.

It is, however, not possible to lower the positive pressure during the exhalation phase in the sense of relieving the apparatus user.

In another known cycle respirator according to German OS No. 31 05 637, the exhalation line is connected to the inhalation line via a $CO_2$ absorber and a gas compensation vessel. A compressed gas bottle containing mostly oxygen communicates with the inhalation line. Best suitable as gas compensation vessel is a bellows with rigid end walls. The bellows is under the force of a cylinder piston unit, continuously acting in the sense of reducing its volume, the piston of which is connected with its end wall and admitted by compressed gas from the compressed gas bottle, expanded to a mean pressure. By the movement of the piston a lasting pressure increase is created in the bellows, sufficient for the desired positive pressure in the entire respiration cycle. By measures not shown in detail, the force acting on the bellows can be varied continuously or intermittently, whereby the pressure prevailing in the cycle can be adapted to the existing operating conditions and the respirator can be set selectively to a negative or a positive pressure operation.

As the force selected and set for the respective use acts continuously and creates a lasting pressure in the respiratory cycle via the piston, this pressure is effective both during the inhalation phase and during the exhalation phase. During exhalation, however, the user must already exert a pressure to overcome the flow resistances in the exhalation valve, lines and $CO_2$ absorber.

By the additionally acting positive pressure he is additionally burdened unnecessarily during the exhalation in an unfavorable manner.

SUMMARY OF THE INVENTION

The present invention provides an improved cycle respirator in which a positive pressure in the respiratory cycle is created only during the inhalation phase, not during the exhalation phase.

In accordance with the invention a sensor, connected with a measuring circuit for determining the respiration phases, is provided, and during the exhalation phase the measuring circuit controls an auxiliary device for reduction of the additional pressure exerted at the breathing bag.

The arrangement of the cycle respirator according to the invention makes it possible for the pressure conditions in the respiration cycle to be controlled as a function of the respiration phases. A sensor provided for determining the respiration phases may be arranged at any desired point of the respiration cycle, as long as it is able to establish the change between the inhalation and the exhalation phase.

Preferably such a sensor is provided at the breathing bag.

In another favorable form of the invention, the compressed gas line is connected by a switching valve with the auxiliary device only during the inhalation phase, but it is shut off during the exhalation phase. At the same time the auxiliary device and the breathing bag are connected together via a connecting line, so that pressure fluctuations due to the stroke movement of the breathing bag can be compensated in the feed line to the auxiliary device. It is indeed possible to connect the feed line to the auxiliary device with the outside atmosphere via the switching valve while the compressed gas line is shut off. Thereby, should pressure fluctuations occur in the exhalation phase, the gas could be blown off out of the feed line. But this would result in the undesired disadvantage that pressure gas, e.g. oxygen, would unnecessarily be lost each time.

Advantageously, the sensor for determining the respiration phase may be designed as an electric resistance path arranged at a guide element connected with the end wall of the piston. Thereby the determination of the respiration phases can be reduced to measuring the direction of movement of the rigid movable wall portion of the breathing bag. The measurement signal to be evaluated by the measuring circuit is supplied by the voltage drop along the measurement path as recorded by a measuring sensor.

Due to the movement of the guide element, the voltage difference to be picked off changes in advantageous manner during a breathing phase, namely by a difference amount $\Delta V_E$ during the inhalation phase, and by a difference amount $\Delta V_A$ during the exhalation phase. Toward the end of a respiration both difference amounts decrease to zero. A change between inhalation phase and exhalation phase means also a change between increase and decrease of the voltage difference $\Delta V_o$ to be picked off. In this way a simple distinguishing criterion is obtained as to when a change takes place between the inhalation phase and the exhalation phase, so that a clear criterion is given to the measuring circuit as to when the switching of the auxiliary device must take place.

If the available voltage difference $\Delta V_o$ itself should reach the value zero, it must be inferred that there is a defect in the respiratory cycle. In that case triggering of an alarm device is desirable.

Accordingly it is an object of the invention to provide an improved respirator having an exhalation line connected to a breathing bag with an inhalation line connected from the breathing bag back to a breathing connection to the patient which also connects the exhalation line and wherein a sensor is provided for measuring the extension and retraction of the breathing bag and for reducing the pressure in the vicinity of the breathing bag during the exhalation phase.

A further object of the invention is to provide a respirator which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
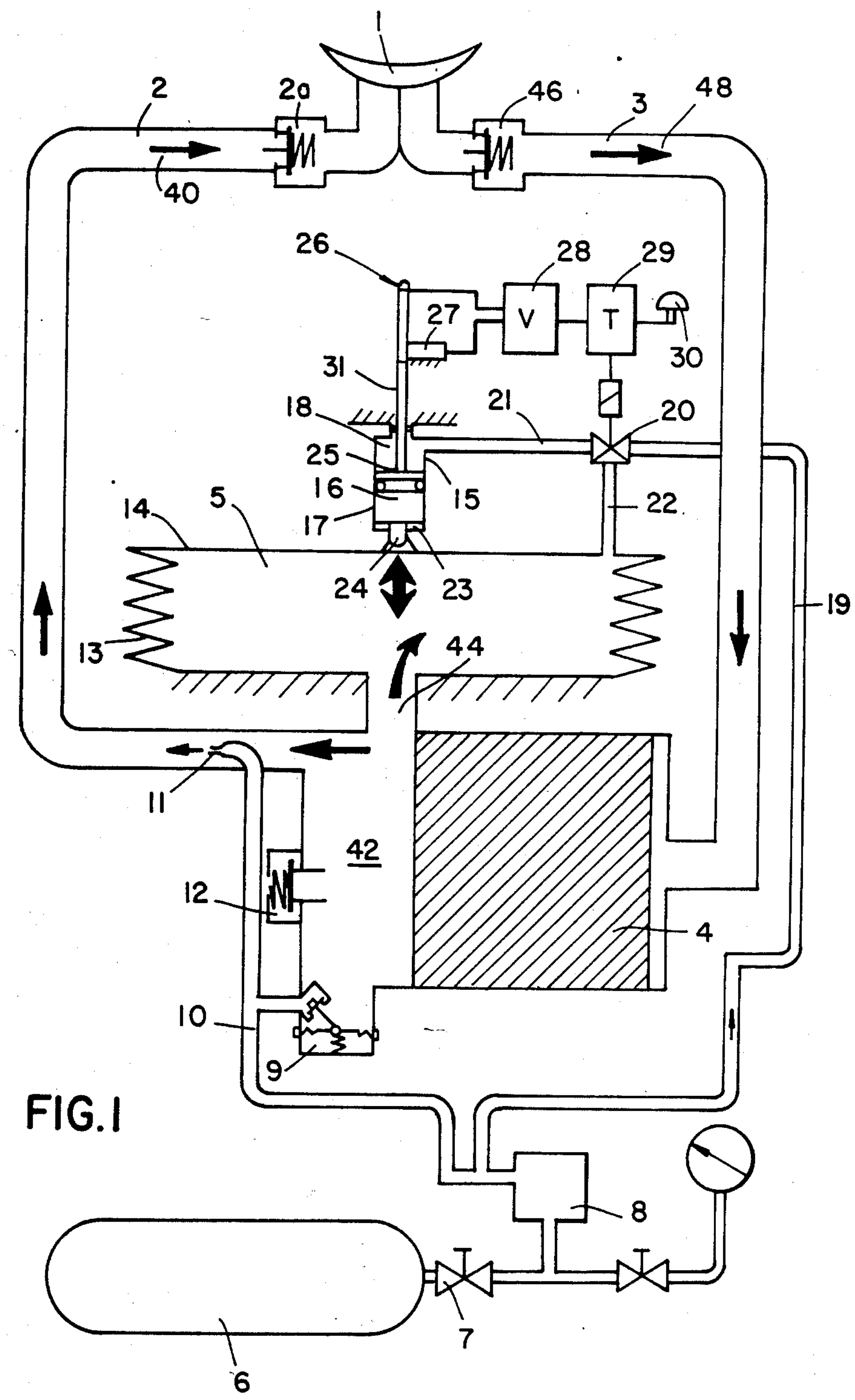
FIG. 1 is a schematic view of a cycle respirator constructed in accordance with the invention.
Figure 2:
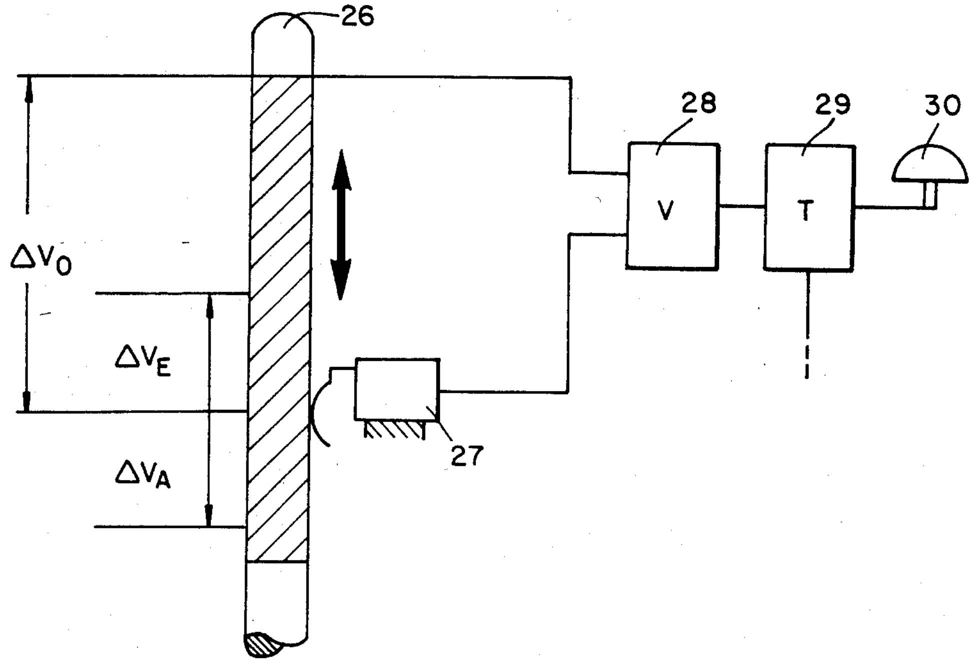
FIG. 2 is an enlarged schematic view of the sensor indicating the differences of voltages to be recorded.

Referring to the drawings in particular the invention embodied therein comprises a respirator which has a breathing connection 1 for connection to a patient. An inhalation line 2 is connected to the breathing connection 1 and extends to an inlet of a breathing bag 5. The inhalation line 2 includes a check valve **2*a* permitting flow in the direction of arrow 40. An exhalation line 3 is connected at one end to the breathing connection 1 and connects into an inlet of a regenerating cartridge 4 which discharges in a passage 42 which connects to inlet 44 of the breathing bag 5. Check valve 46 permits flow in the direction of arrow 48**.

In accordance with the invention, sensor means generally designated 26 senses the operation of the breathing bag 5 and it is connected to means in the form of a pressure discharge nozzle 11 for reducing the pressure in the vicinity of the breathing bag during exhalation. The sensor includes a measuring circuit with elements 28,29 and 30 for determining the respiration phases which are taking place so as to control an auxiliary device 15 which is responsive to the movement of a wall 14 of the breathing bag 5 to influence the pressure conditions at the inlet 44 into chamber 42.

The cycle respirator with pressure operation contains the components forming the respiratory cycle, shown in functional arrangement, on a carrying structure in a protective covering. They are breathing connection 1, exhalation line 3, regeneration cartridge 4 binding the carbon dioxide present in the exhaled air, breathing bag 5, and inhalation line 2.

The oxygen consumed during respiration is supplied from a pressurized supply 6 to the respiratory cycle bottle valve 7, a pressure reducer 8 via a lungmotor 9 and via a conduit 10 to the discharge nozzle which acts as a constant dosage device 11 behind the breathing bag 5. An overpressure valve 12 behind the regeneration cartridge 4 prevents too high a pressure in the respiratory cycle.

The breathing bag 5 consists of a bellows 13 which is closed off by a movable rigid end wall 14. A cylinder-piston unit forms device 15. It has a piston 16 in a cylinder 17 that forms, above the piston 16 a pressure chamber 18, which is connected to the conduit 10 via a pressure line 19. Pressure line 19 contains a solenoid valve 20 which forms control means and with which the pressure line 19 is closed and in so doing a line portion 21 before the pressure chamber 18 is separated off, which then can be connected with the breathing bag via the line portion 21 and a connecting line 22.

By its lower end face 23 opposite the pressure chamber 18, piston 16 protrudes from the cylinder 17 which is open to that side and is connected via a movable connection 24 with the end wall 14 of the breathing bag 5.

At the upper piston end wall 25 to the pressure chamber 18, a sensor 26 is fastened axially on a guiding element 31. Sensor 26 is designed as an electric resistance path which on the input side is connected with the amplifier 28. A current impressed by the amplifier creates along the resistance path a voltage drop, which is sensed by a stationary wiper contact 27. The voltage differences $\Delta V_E$, $\Delta V_A$ and $\Delta V_o$ determined with a transmitter 29 furnish the switching values for the solenoid valve 20. The respiration phases, that is, the inhaling and the following exhaling, lead to repetitive functions and pressure conditions in the respiratory cycle.

In the inhaling phase, solenoid valve 20 opens to connect the pressure chamber 18 with conduit 19. The positive pressure resulting therein from the pressure reducer 8 propagates into the pressure chamber 18, presses on the piston 16, and moves the latter and hence the end wall 25 thereof downward. In the area ratio of piston end wall 25 to end wall 14 of the breathing bag 5 the pressure develops the position pressure in the respiration cycle. The positive pressure exists during the total inhalation phase and prevents the penetration of possibly unbreathable ambient atmosphere into the respiration cycle. The movement of sensor 26 simultaneous with piston 16, involving a varying length of the resistance path to the wiper contact 27, leads to a voltage difference $\Delta V_o$ decreasing by $\Delta V_E$. At a voltage difference $\Delta V_E=0$, that is, at the end of the inhalation phase (end of breathing in), the solenoid valve 20 is closed and thus the pressure line 19 is separated from the pressure chamber 18. The pressure chamber 18 is then connected with the breathing bag 5 via line portion 21 and the connecting line 22. The positive pressure created in the respiratory cycle via piston 16 is abolished by relaxation in pressure chamber 18.

With the start of exhalation, during which there is no positive pressure in the respiratory cycle, the breathing bag 5 expands upward and moves the end wall 14 accordingly. Bag 5 is filled by gas from exhalation line 3 which passes through cartridge 4, passage 42 and inlet 44. The resistance path on sensor 26 becomes longer again. There occurs an increase of the voltage difference $\Delta V_0$ by the amount $\Delta V_A$, which changes with the movement. At end of exhalation, at a large breathing bag volume and a voltage difference $\Delta V_A = 0$, solenoid valve 20 switches to open again, so that for the then following inhalation phase the positive pressure can build up again in the respiratory cycle.

As noted previously, the sensor 26 determines the change between the inhalation phase and the exhalation phase by determining the change between the increasing of the voltage difference and the decreasing of the voltage difference. In other words, if the voltage difference has been increasing for a certain time, then starts to decrease, the point at which the voltage difference starts to decrease is interpreted as the beginning of the exhalation phase. It is noted that the person using the equipment, by the function of breathing, initiates the inhalation and exhalation phases, one after the other. These phases are then sensed by the sensor 26 and then used to control valve 20.

In case of severe defect (leak) developing in the respiratory cycle, the positive pressure therein decreases completely. The still existing oxygen pressure in pressure line 19 with the solenoid valve 20 open (line 19 connected to line 21) compresses the breathing bag to a large extent. With the voltage difference $\Delta V_0 = 0$ at the then shortest resistance path, solenoid valve 20 closes (line 19 connected to line 22). Because it has no inherent elasticity, the breathing bag 5 remains in the position in which it is smallest, solenoid valve 20 remains closed relative to the pressure line 19 permanently, and at the same time an alarm system 30 goes into operation. With a major leak in the system, exhalation gas from line 3 will not fill bag 5. The apparatus user can now use the cycle respirator over lung motor 9 with normal pressure. His oxygen supply occurs via conduit 10 in the normal manner. After the closing of the defect (leak), the respiratory cycle automatically switches to pressure operation again as the breathing bag 5 fills up again.

While a specific embodiment of the invention has been shown and described in detail to illustrate the application of the principles of the invention, it will be understood that the invention may be embodied otherwise without departing from such principles.

What is claimed is:

1. A respirator comprising an extendable and retractable breathing bag having an inlet, an exhalation line having one end connected to said inlet, an inhalation line having one end connected to said inlet, a breathing connection for a patient connected to opposite ends of said inhalation and exhalation lines, a compressed gas source connected to said inhalation line for supplying a compressed gas thereto to apply an initial pressure to said bag, an auxiliary device having a movable part engaged with said bag for applying additional pressure to said bag in one direction only during the inhalation phase, said movable part moving in one direction to provide said additional pressure and collapse the bag during the inhalation phase and in an opposite direction during extension of the bag during the exhalation phase, a compressed gas line having one end connected to said compressed gas source and an opposite end connectable to said auxiliary device for supplying compressed gas under pressure to said movable part to move said movable part in said one direction to apply the additional pressure to said bag, a sensor operatively connected to said movable part for sensing movement in said one and said opposite directions of said movable part, and control means connected to said sensor, said auxiliary device and to said compressed gas line, said control means being responsive to a change in movement of said movable part from said one direction to said opposite direction to indicate initiation of an exhalation phase, and being responsive to a reversal of direction from said opposite direction to said one direction to indicate initiation of the inhalation phase, said control means connecting said compressed gas line to said auxiliary device at initiation of the inhalation phase and disconnecting said compressed gas line from said auxiliary device at the initiation of the exhalation phase to remove the additional pressure applied by said auxiliary device to said bag during the exhalation phase.

2. A respirator according to claim 1, wherein said auxiliary device comprises a cylinder and piston unit forming said movable part and operatively connected to said bag, said control means comprising a switching valve connected between said compressed gas line and said cylinder and piston unit, said switching valve being operable by said sensor during the exhalation phase to shut off flow from said compressed gas line to said cylinder and piston unit, and a connecting line connected between said switching valve and said breathing bag for establishing communication between said cylinder and piston unit and said breathing bag when said switching valve is switched during the exhalation phase.

3. A respirator according to claim 2, wherein said cylinder and piston unit comprises a cylinder having a pressure chamber connected to said switching valve and a cylinder movable in said pressure chamber and connected to said breathing bag.

4. A respirator according to claim 3, wherein said sensor comprises a guide element fixed to said piston and movable with said piston, said bag having a movable wall which is movable in a first direction to retract the bag and reduce its volume, and an opposite second direction to extend said bag and increase its volume, said piston being connected to said movable wall for movement with said movable wall, said pressure chamber of said cylinder being connected to said compressed gas line for receiving compressed gas over said switching valve during the exhalation phase for enlarging said pressure chamber to move said piston and said movable wall in said first direction, said sensor including a fixed wiper contact engaged with said guide element, said guide element having a fixed location thereon which defines a resistance path with said wiper contact, said resistance path changing with movement of said guide element, said control means comprising an amplifier connected between said fixed location on said guide element and said wiper contact for measuring a voltage drop on said resistance path, said control means also including a transmitter connected between said amplifier and said switching valve for operating said switching valve according to the value of said voltage drop, said guide element being movable to a first position after completion of the exhalation phase with said bag partly retracted to initiate an inhalation phase, said guide element being movable to a second position upon completion of the inhalation phase with said bag extended to initiate a subsequent exhalation phase.

5. A respirator according to claim 4, wherein said guide element is movable to a third position when a leak develops in said respirator, said third position resulting from said bag being fully retracted beyond said partial retraction of said bag at said first position of said guide element, the voltage drop across said resistance path when said guide element is in its third position causing said transmitter to form a signal which maintains said switch valve in a condition disconnecting said compressed gas line from said pressure chamber, and alarm means connected to said transmitter responsive to said signal to activate an alarm, said alarm being indicative of said bag being fully retracted and the occurrence of a leak in said respirator.

6. A respirator according to claim 3, wherein said sensor contains an electric resistance path and means for picking off a voltage difference from said resistance path during operation of said breathing bag.

7. A respirator according to claim 6, including a guide element containing said electrical resistor path and connected to said piston.

8. A respirator according to claim 6, where in the course of inhalation the voltage difference changes by an amount which diminishes to zero and in the course of exhalation by an amount which also diminishes to zero, and that such amounts have opposite signs and including a measuring circuit connected to said sensor and to said switching valve for connecting gas under pressure to said inhalation line between inhalation and exhalation phases when the sign changes the measured amounts after they reach zero.

* * * * *